US006635874B1

(12) United States Patent
Singh et al.

(10) Patent No.: US 6,635,874 B1
(45) Date of Patent: Oct. 21, 2003

(54) SELF-CLEANING TECHNIQUE FOR CONTAMINATION ON CALIBRATION SAMPLE IN SEM

(75) Inventors: Bhanwar Singh, Morgan Hill, CA (US); Michael K. Templeton, Atherton, CA (US); Sanjay K. Yedur, San Ramon, CA (US); Bryan K. Choo, Mountian View, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 415 days.

(21) Appl. No.: 09/729,290

(22) Filed: Dec. 4, 2000

Related U.S. Application Data
(60) Provisional application No. 60/242,757, filed on Oct. 24, 2000.

(51) Int. Cl.[7] .................................................. G21K 7/00
(52) U.S. Cl. ...................................................... 250/311
(58) Field of Search .................... 356/243.9; 250/252.1, 250/311, 306; 438/743, 753, 756

(56) References Cited

U.S. PATENT DOCUMENTS

| | | | | |
|---|---|---|---|---|
| 4,766,311 A | * | 8/1988 | Seiler ..................... | 250/252.1 |
| 4,788,117 A | * | 11/1988 | Cuthbert ..................... | 430/30 |
| 5,308,454 A | | 5/1994 | Anderson ................. | 204/59 R |
| 5,756,207 A | | 5/1998 | Clough et al. .............. | 428/375 |
| 6,094,256 A | | 7/2000 | Grodnensky et al. ......... | 355/77 |
| 6,358,860 B1 | * | 3/2002 | Scheer ....................... | 438/745 |
| 6,420,703 B1 | * | 7/2002 | Wu ............................. | 250/311 |
| 6,459,482 B1 | * | 10/2002 | Singh ....................... | 356/243.1 |

OTHER PUBLICATIONS

"A Novel Catalyst for CO Oxidation at Low Temperature," Guoli Dong, et al., J.C. Baltzer AG, Science Publishers, Catalysis Letters, 58 (1999) 37–41.

* cited by examiner

*Primary Examiner*—John F. Niebling
*Assistant Examiner*—Andre' C Stevenson
(74) *Attorney, Agent, or Firm*—Amin & Turocy, LLP

(57) ABSTRACT

The present invention provides SEM calibration standards, and associated SEM systems and SEM calibration methods, that are self-cleaning with respect to electron beam deposited carbon. The calibration standards have coatings containing a transition metal oxide. The coatings facilitate oxidation of deposited carbon, whereby carbon buildup can be stopped or reversed. By providing a mechanism to mitigate carbon buildup, calibration standards provided by the present invention achieve high accuracy, high durability, and low cost.

25 Claims, 3 Drawing Sheets

SELF-CLEANING TECHNIQUE FOR CONTAMINATION ON CALIBRATION SAMPLE IN SEM

RELATED APPLICATIONS

This application claims domestic priority to provisional application Ser. No. 60/242,757 filed Oct. 24, 2000.

TECHNICAL FIELD

The present invention relates to nanometerology and in particular to calibration methods, calibration standards, and systems for critical dimension scanning electron microscopy.

BACKGROUND OF THE INVENTION

In the semiconductor industry, there is a continuing trend toward higher device densities. To achieve these higher device densities there have been, and continue to be, efforts toward scaling down the device dimensions on semiconductor wafers. In order to accomplish higher device densities, smaller and smaller features sizes are required. These may include the width and spacing of interconnecting lines, spacing and diameter of contact holes, and surface geometry of corners and edges of various features.

High resolution lithographic processes are used to achieve small features. In general, lithography refers to processes for pattern transfer between various media. In lithography for integrated circuit fabrication, a silicon slice, the wafer, is coated uniformly with a radiation-sensitive film, the resist. The film is selectively exposed with radiation (such as optical light, x-rays, or an electron beam) through an intervening master template, the mask, forming a particular pattern. Exposed areas of the coating become either more or less soluble than the unexposed areas (depending on the type of coating) in a particular solvent developer. The more soluble areas are removed with the developer in a developing step. The less soluble areas remain on the silicon wafer forming a patterned coating. The pattern corresponds to the image of the mask or its negative. The patterned resist is used in further processing of the silicon wafer.

At various stages in forming the patterned resist coating and processing the silicon wafer, it is desirable to measure critical dimensions resulting from the lithographic process. Critical dimensions include the size of features in the wafer or patterned resist such as line widths, line spacing, and contact dimensions. Due to the extremely fine patterns involved, scanning electron microscopy (SEM) is often employed to analyze critical dimensions. Specialized critical dimension measuring SEM systems have been developed for use with silicon wafers, which are of a size that makes them too large for most SEM systems.

In SEM, an electron beam is scanned across the sample. The beam interacts with the sample to produce measurable responses that vary with position over the course of a scan. Measurable responses include backscattering of electrons and production of secondary electrons, auger electrons, X-rays and cathodoluminescence. Secondary electrons are the most useful of the measurable responses in accessing surface topography and are the responses most often employed in critical dimension analysis.

Although SEM systems measure critical dimensions with high precision, they must be calibrated frequently for the measurements to be accurate. Precision refers to the capability of distinguishing small differences in dimension. Accuracy refers to the correctness of measurements in absolute terms. Precise measurements are reproducible, but contain systematic errors that must be quantified and taken into account for the measurements to be accurate. Calibration quantifies systematic errors and is carried out on a regular basis in SEM systems, usually at least once a day.

Calibration involves taking measurements on a calibration standard. A calibration standard is a sample having accurately known dimensions. One calibration standard commonly employed is a periodic pattern formed into a silicon substrate. Such a calibration sample is simple, but has low contrast and easily becomes contaminated over the course of extended use.

Another type of calibration standard is formed with a patterned polysilicon coating over a silicon wafer. A thin layer of silicon oxide is used to facilitate binding between the patterned polysilicon and the wafer. A similar calibration standard is formed with a uniform polysilicon coating over the silicon oxide layer and has a calibration patterned formed in another silicon oxide coating that is formed over the polysilicon. These calibration standards can be used with very low electron beam energies, however, due to the insulating properties of the silicon oxide, at higher beam energies these calibration standards undesirably accumulate charges that affect the electron beam and skew calibration measurements.

Another calibration standard, described in Yang et al., U.S. Pat. No. 6,048,743, includes a semiconductor wafer, an insulating first patterned layer formed on the wafer, a plurality of contacts electrically communicating with the wafer and formed between the pattern of the first insulating layer, a conductive layer formed over the first insulating layer and in electrical communication with the wafer through the contacts, and a second insulating layer with a second pattern formed over the conductive layer. The conductive layer electrically communicates between the second insulating layer and the wafer and permits charges to drain from the second insulating layer to the wafer during scanning. An example is provided in which the second insulating layer is polysilicon.

During calibration scanning, the electron beam causes carbon to deposit on the calibration standard. Deposited carbon changes the sample dimensions, thus affecting the accuracy of the calibration. While carbon deposition can be dealt with by periodic replacement of the calibration standard, this raises the cost of the calibration standard. There remains an unsatisfied need for SEM system calibration standards and calibration methods with high accuracy an low cost.

SUMMARY OF THE INVENTION

The present invention provides SEM calibration standards, and associated SEM systems and SEM calibration methods, that are self-cleaning with respect to electron beam deposited monolayer of carbon contaminents. The calibration standards have coatings containing a transition metal oxide. The coatings facilitate oxidation of deposited carbon, whereby carbon buildup can be stopped or reversed. By providing a mechanism to mitigate carbon buildup, calibration standards provided by the present invention achieve high accuracy, high durability, and low cost.

One aspect of the invention provides a calibration standard for a SEM system including a substrate having a surface on which are formed patterned features having dimensions suitable for calibrating the SEM system, wherein the patterned features include a coating of a material containing a transition metal oxide.

Another aspect of the invention provides a calibration standard for a SEM system including means for removing carbon deposits that form on the calibration standard during calibration scanning.

A further aspect of the invention provides a method of calibrating a SEM system including obtaining a calibration measurement by employing the SEM system to measure a dimension of a feature of a calibration standard, wherein the feature includes a coating of a material containing a transition metal oxide and using the calibration measurement to calibrate the SEM system.

A further aspect of the invention provides a SEM system including a scanning electron microscope and a calibration standard having patterned features including a coating containing a transition metal oxide, wherein the SEM system is configured to employ the calibration standard in calibrating the scanning electron microscope.

DETAILED DESCRIPTION OF THE INVENTION

Figure 1:
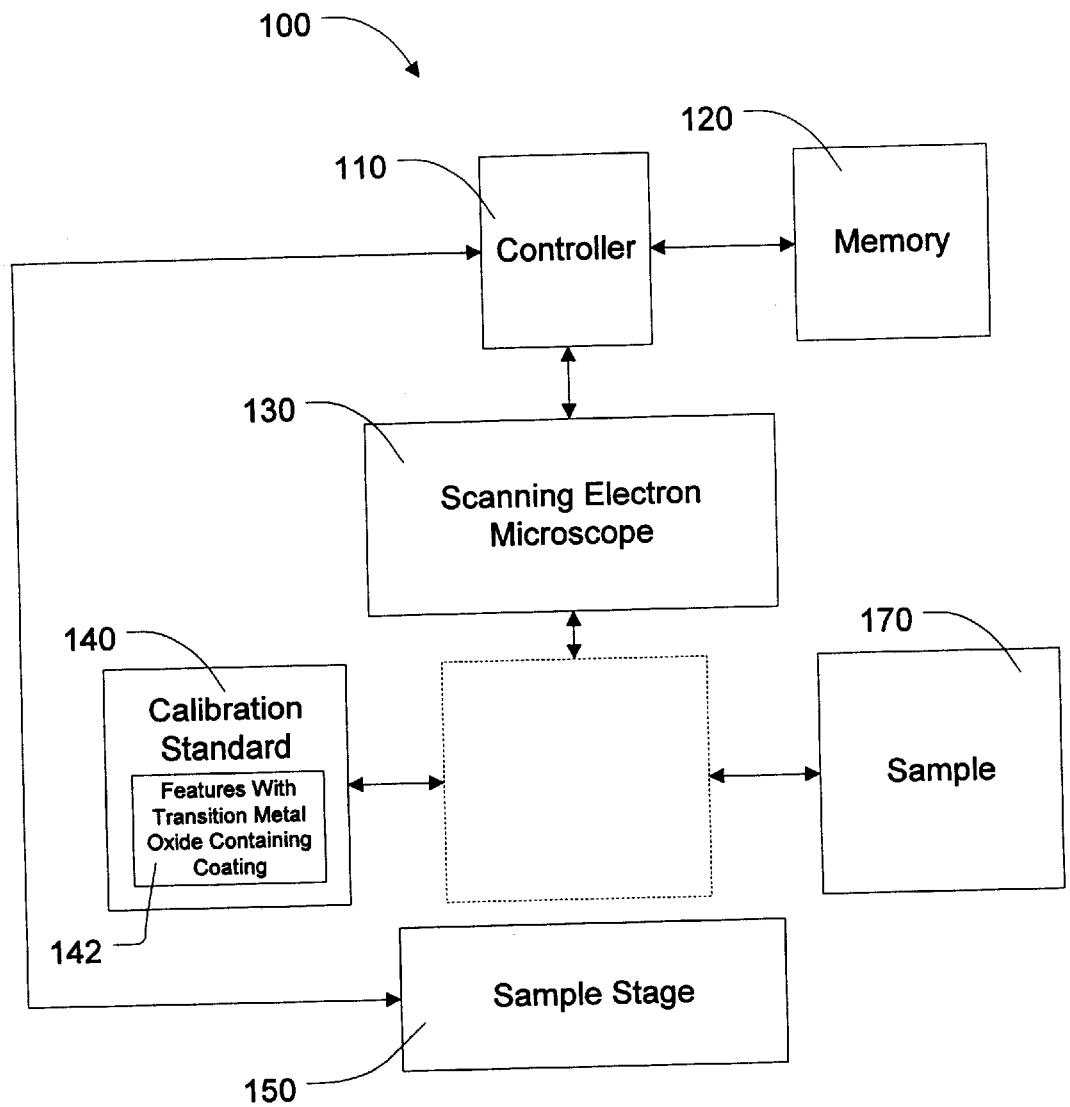
FIG. 1 is a high level schematic of a SEM system according to one aspect of the present invention.

FIG. 1 is a high level schematic illustration of a SEM system 100 according to one aspect of the present invention. SEM system 100 includes scanning electron microscope 130, sample stage 150, calibration standard 140, controller 110, and memory 120. SEM system 100 is calibrated by placing calibration standard 140 on sample stage 150 and scanning calibration standard 140 with scanning electron microscope 130. Controller 110 stores the calibration data in memory 120 and uses the data to interpret data obtained by scanning sample 170 of which an accurate measurement is sought.

Calibration standard 140 includes a pattern suitable for use in calibrating a SEM system. A suitable pattern may include features, such as raised lines, trenches, or holes, of predetermined size, width, and/or spacing. The pattern may include periodic or non-periodic features. For example, the pattern may include a series of raised lines with predetermined pitch, or a series of lines with predetermined but varying spacing. In one aspect of the invention, the calibration standard has periodic features with a pitch less than about 1 micron. In another aspect of the invention, the calibration standard has periodic features with a pitch less than about 200 nm. In a further aspect of the invention, the calibration standard has periodic features with a pitch less than about 50 nm.

Calibration standard 140 has a coating that includes a transition metal oxide. Examples of transition metal oxides include Group IVa metal oxides, Group Va metal oxides, Group VIa metal oxides, Group VIIa metal oxides, Group VIII metal oxides, Group Ib metal oxides, and Group IIb metal oxides. Specific examples of transition metal oxides include $TiO_2$, $Cr_2O_3$, $CrO_3$, $MoO_2$, $MoO_3$, $WO_2$, $WO_3$, $MnO_2$, $MnO_3$, $Fe_2O_3$, $Co_3O_4$, NiO, CuO, ZnO, $In_2O_3$, SnO, and $SnO_2$. The coating may be conductive or non-conductive. The coating may include dopants that increase conductivity. Examples of such dopants include halogen compounds, such as fluorides and chlorides, alumina, cobalt, gallium, titanium, indium, tin, and germanium.

While not wishing to be bound by any theory, it is believed that the transition metal oxide containing coating mitigates carbon deposition by promoting oxidation of deposited carbon and/or preventing carbon deposition from taking place. Where the coating is conductive, the mechanism of carbon deposition mitigation usually involves either applying a positive electrical potential to the coating to electrochemically promote oxidation or flowing a current through the coating to promote oxidation through the application of heat. Alternatively, the transition metal oxide may act as an oxidation catalyst. In one aspect of the invention, the transition metal oxide is a photocatalyst.

In general, the oxidation rate of carbon increases with increasing temperature. Resistive heating of a conductive transition metal oxide contain coating thereby induces oxidation of deposited carbon. Calibration standard 140 may be provided with two electrical contacts adapted to attach leads from a power source to calibration standard 140, whereby a current, generally a DC current, may be passed through the transition metal oxide containing coating. Alternatively, induction may be used to produce resistive heating within a conductive coating.

The calibration standard may promote oxidation of carbon electrochemically. Setting the coating to a suitable positive electrical potential promotes the oxidation reaction. A single electrical contact may be provided to facilitate setting the coating to a positive electrical potential. Generally, a counter electrode is provided for electrochemical oxidation of carbon, however, an electron beam may function as a counter electrode.

The transition metal oxide may also, or alternatively, act as an oxidation catalyst. Particularly well suited are low temperature oxidation catalyst. Examples of low temperature oxidation catalysts include $TiO_2$ doped with Pd, $SnO_2$ doped with Pt, and $Fe_2O_3$, $Co_3O_4$, $TiO_2$, NiO or $MnO_x$ doped with Au.

The transition metal oxide may specifically be a photocatalyst, such as $TiO_2$, particularly $TiO_2$ in the anatase or rutile form. A photocatalyst promotes oxidation after irradiation with ultraviolet light with an energy above the band gap energy. The transition metal oxide photocatalyst may be irradiated either before or after electron beam scanning.

Features of the calibration standard may be formed in the transition metal oxide containing coating or features formed of another material may be coated with the transition metal oxide containing coating. Where the transition metal oxide containing coating coats a calibration pattern formed in another material, the transition metal oxide coating is thin. In one aspect of the invention, the thickness of the transition metal oxide coating is from about 1 nm to about 1000 nm. In another aspect of the invention, the thickness of the transition metal oxide coating is from about 1 nm to about 100 nm. In a further aspect of the invention, the thickness of the transition metal oxide coating is from about 10 nm to about 50 nm.

Features of the calibration standard are generally formed over a substrate. The substrate may be of any type, conductor, semi-conductor, or insulator. Where the transition metal oxide containing coating is non-conducting, it is desirable for the substrate to be conducting or semi-conducting and for the features of calibration standard 140 to be grounded to the substrate to prevent accumulation of charges during electron beam scanning. The substrate itself may be grounded to sample stage 150. Where the coating is conductive, the coating itself may be grounded to sample stage 150.

The substrate may be of any shape that fits within a sample chamber of electron microscope 130. For example, the substrate may be a silicon wafer that conveniently fits in the sample holder of a CD-SEM adapted for use in measuring critical dimensions on silicon wafers.

Where the features of the substrate are not formed of the transition metal oxide containing material, the feature may be formed of any convenient material, such as amorphous silicon or polysilicon. Amorphous silicon or polysilicon features can be bound to a silicon wafer substrate through an intermediate layer of material, such as silicon dioxide. Where the intermediate layer contains an insulating material, such as silicon dioxide, the intermediate layer may be patterned with gaps to provide for electrical communication between the calibration features and the silicon wafer. Electrostatic charges imparted to the calibration features during electron beam scanning may thereby drain to the silicon wafer rather than accumulating to a level where they may distort the electron beam. Alternatively, where the transition metal oxide containing coating is conductive, charges may be drained through the transition metal oxide containing coating.

The transition metal oxide containing coating may be formed by any suitable method, including, for example, chemical vapor deposition (CVD), physical vapor deposition (PVD), spray pyrolysis, sol gel technique, spin coating a solution containing the corresponding metal salt, or sintering. Alternatively, a coating of the corresponding metal may be formed by one of the forgoing methods and at least the outer surface of the metal oxidized to form the transition metal oxide.

Generally, it is desirable to avoid forming large crystallites in the transition metal oxide containing coating. Large crystallites may increase the roughness of feature edges and reduce the accuracy of the calibration standard. $R_{tm}$, a measure of surface roughness, is the mean of the maximum peak-to-valley vertical measurement from each of five consecutive sampling measurements, and can be measured using known techniques including using one of an atomic force microscope and a scanning electron microscope. A rough surface is characterized by "mountainous" features (numerous peaks and valleys) and/or dendritic features. In one aspect of the invention, the transition metal oxide containing coating has an $R_{tm}$ of about 100 Å or less. In another aspect of the invention, the transition metal oxide containing coating has an $R_{tm}$ of about 50 Å or less.

Figure 2:
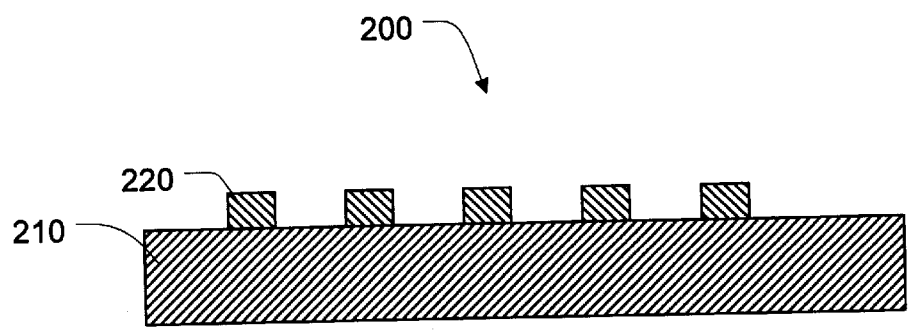
FIG. 2 is a cross-sectional schematic illustration of a calibration standard according to another aspect of the present invention.

The features of calibration standard 140 may be patterned in the transition metal oxide containing coating using lithography. FIG. 2 provides a cross-sectional illustration of such a calibration standard. Calibration standard 200 has transition metal oxide containing coating 220, which has been patterned to form a series of raised lines over substrate 210. Either transition metal oxide containing coating 220 or substrate 210 is conducting or semi-conducting and may be grounded to the sample stage during SEM system operation.

The transition metal oxide containing coating may be bound directly to the substrate, as illustrated by calibration standard 200. Alternatively, transition metal oxide containing coating can be bound to the substrate through an intermediate layer. For example, a transition metal oxide containing coating can be formed over a silicon wafer substrate and bound thereto through an intermediate layer of material, such as silicon dioxide. Where the intermediate layer contains an insulating material, such as silicon dioxide, the intermediate layer may be patterned with gaps to provide for electrical communication between the transition metal oxide containing coating and the substrate. Electrostatic charges imparted to the transition metal oxide containing coating and during electron beam scanning may thereby drain through the substrate.

Figure 3:
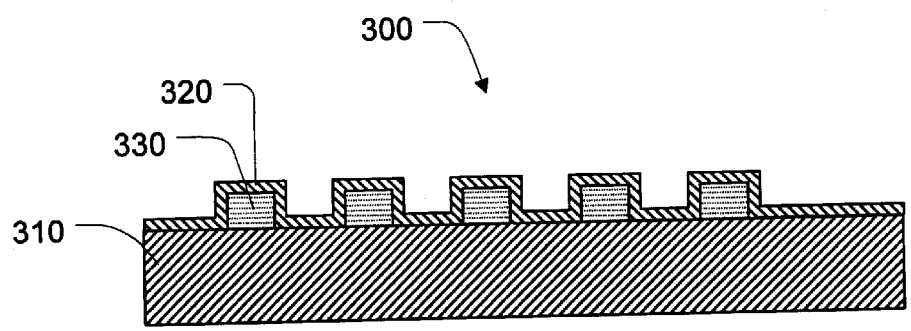
FIG. 3 is a cross-sectional schematic illustration of another calibration standard according to a further aspect of the present invention.

The features of calibration standard 140 may be patterned in a material other than the transition metal oxide containing coating. FIG. 3 provides a cross-sectional illustration of such a calibration standard. Calibration standard 300 has transition metal oxide containing coating 320 formed over first patterned coating 330. First patterned coating 330 includes a series of raised lines formed over substrate 310. First patterned coating 330 may be formed, for example, by lithographic patterning of a coating that contains silicon dioxide or polysilicon.

Figure 4:
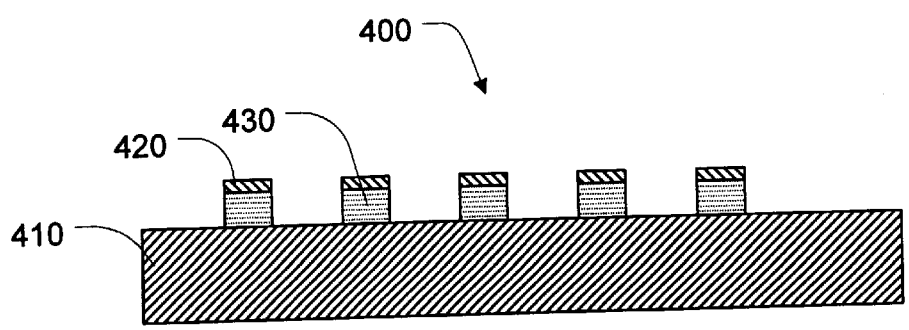
FIG. 4 is a cross-sectional schematic illustration of another calibration standard according to a further aspect of the present invention.

FIG. 4 provides a cross-sectional illustration of an alternative form for calibration standard 140 in which the transition metal oxide containing coating covers a portion of a surface of a substrate. Calibration standard 400 has transition metal oxide containing coating 420 formed over a primary coating 430. Primary coating 430 and transition metal oxide containing coating 420 have been patterned together through lithography. Transition metal oxide containing coating 420 cover the upper surfaces of raised lines of the patterned coating, but is not found in the trenches between raised lines. Over the course of SEM system calibration, carbon may build up in the trenches. However, the upper dimensions of the raised lines still remains fixed, particularly where lithography has provided the raised lines with reentrant profiles.

Returning to FIG. 1, the calibration standard 140 is used in system 100 with scanning electron microscope 130. Scanning electron microscope 130 may detect backscattered electrons, interference of backscattered electrons, secondary electrons, auger electrons, X-rays or cathodoluminescence. In operation of system 100, an electron beam is scanned across calibration standard 140 or sample 170 and a response that varies with position over the course of a scan is measured. Scanning is generally effectuated by varying the angle of the electron beam, although scanning may also be effectuated by moving sample stage 150. In either case, calibration provides a relationship between the measured relative movement of the electron beam and the sample and their actual relative movement. Calibration may also be used to take into account such factors as the effect of electron beam cross-sectional dimensions in measuring sample critical dimensions.

Scanning, calibration, and cleaning of carbon from calibration standard 140, or a combination of the foregoing, may take place under the direction of controller 110. Controller 110 receives data from scanning electron microscope 130 and, in some cases, sample stage 150. Where the data includes measurements from sample 170, controller 110 may transmit the data, store the data in memory 120, and/or interpret the data in view of calibration measurements. Where the data concerns calibration standard 140, controller 110 may transmit the data, store the data in memory 120, and/or interpret the data to calibrate scanning electron microscope 130.

Controller 110 typically includes a microprocessor, but may be any device that is capable of applying calibration data to scale or interpret measurements from the nano-scale measuring device 130. Controller 110 may be analog or digital. If controller 110 is digital, its instructions may be implemented in either hardware or software.

Controller 110 may be configured to calibrate scanning electron microscope 130 in response to an instruction, which may be provided by a user or may be generated automatically based on the passage of time, whether the system has recently been powered on, or any other circumstance that may indicate the need for calibration. As part of the calibration, controller 110 may accept as an input dimensional data regarding features of calibration standard 140. The calibration process involves scanning calibration standard 140 and storing or interpreting the calibration data to adjust scanning electron microscope 130 or interpret measurements of sample 170. The scan, or sequence of scans, of the calibration standard my be directed by controller 110 as part of the calibration process. Controller 110 may also direct the loading of calibration standard 140 onto sample stage 150. The direction may be sent to a user or implemented through an automatic sample loading system, where system 100 is provided with such a sub-system.

Controller 110 may also be configured to direct cleaning of calibration standard 140. Such directions may involve flowing a current through the transition metal oxide containing coating, setting the transition metal oxide containing coating to a positive potential, or exposing the transition metal oxide containing coating to ultraviolet light. Alternatively, an operator may be directed to perform one of the forgoing operations based on data regarding usage of calibration standard 140.

Figure 5:
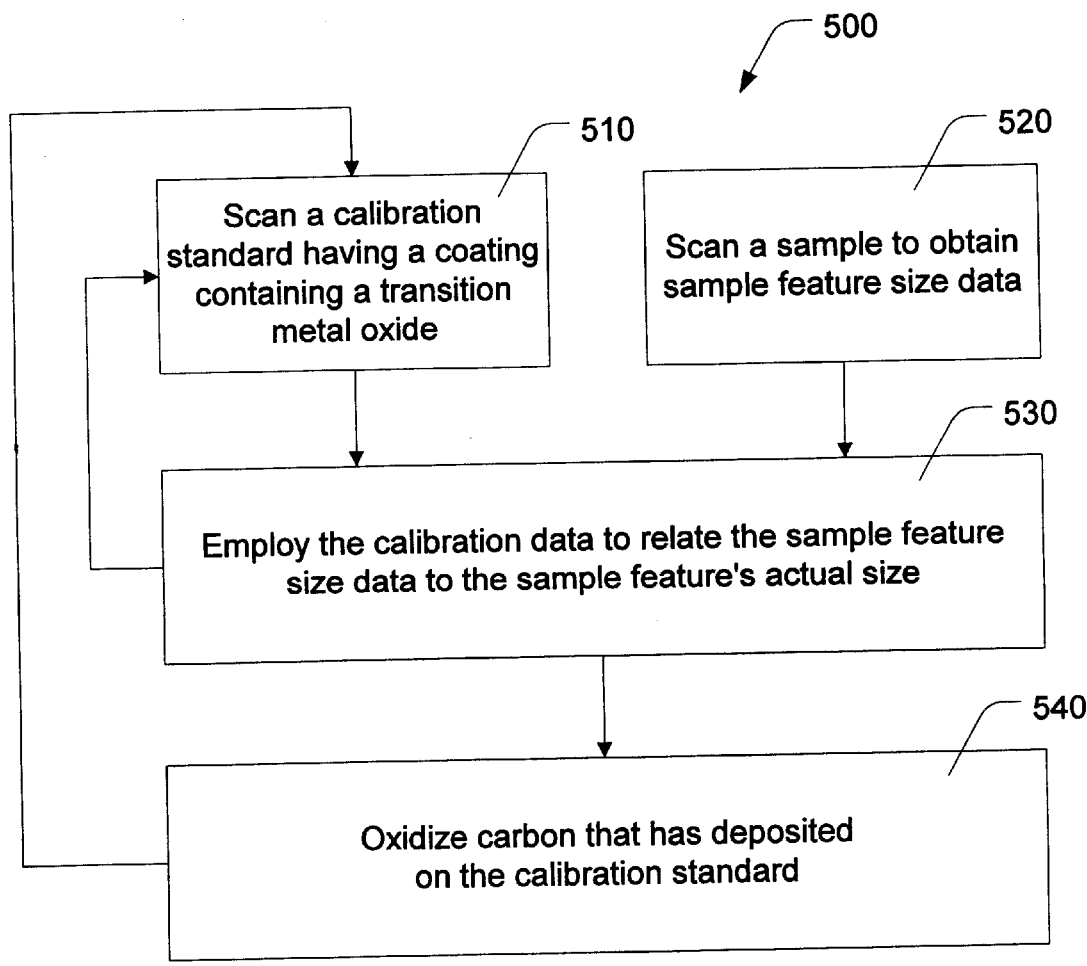
FIG. 5 is a flow diagram of a process according to a further aspect of the present invention.

FIG. 5 is a flow diagram of a process 500 of calibrating a scanning electron microscope according to one aspect of the present invention. In step 510, a calibration standard having a coating containing a transition metal oxide is scanned to obtain calibration data related to the scanning electron microscope. In step 540, which may take place during step 510, carbon that has deposited on the calibration standard is oxidized. In step 520, which may take place before or after step 510, a sample is scanned to obtain sample feature size data. The feature size data may be, for example, data relating to the size of a topographic feature, such as the width of a raised line or the width of a trench. The data could also relate to a non-topographic feature, such as the width of a conductive region. In step 530, the calibration data and a known dimension of the calibration standard are used to relate the measured sample feature size data to the sample feature's actual size.

There are several options for carrying out step 530. In the simplest case, a feature that gives a measured size the same as that of the calibration standard is determined to have the same size as the calibration standard. Generally, however, the size measured for the sample is not the same as the size measured for the calibration standard. Therefore, an interpolation or extrapolation takes place. For example, the calibration data may be used to compute a proportionality factor, a, between measured values $V_M$ and actual values $V_A$, such that:

$$V_A = aV_M$$

Alternatively, the calibration may be used to compute an offset factor, b, such that:

$$V_A = V_M + b$$

Or, using two or more calibration measurements, a two factor linear relationship may be developed:

$$V_A = aV_M + b$$

Other relationships, including relationships with greater numbers of parameters, may also be used. The relationship may take into account, for example, variations in the calibration measurement that depend on the positioning of the measured feature in the scanning electron microscope. Rather than expressing the calibration relationship as a function, the calibration data may be stored in a table, for example, and measurements looked up against the table, interpolating where measurements fall between table entries.

The application of calibration data to interpretation of feature size measurements may take the form of a model, such as a model of electron beam dimensions (diameter, major and minor elliptical axis, etc.). In this regard, the calibration may be broken down into several elements. For example, one calibration may be used to relate measured relative movement of the electron beam and sample to actual relative movement, while another calibration may be used to characterize the electron beam cross-sectional shape and correct feature size measurements for beam shape effects. The calibration may be applied by adjusting the SEM system or the calibration may be applied in processing data from the SEM system.

There are also several options for carrying out step 540, the step of oxidizing carbon that deposits on the calibration standard. In one aspect of the invention, step 540 involves flowing a current through the transition metal oxide coating. In another aspect of the invention, step 540 involves setting the transition metal oxide coating to a positive potential. In a further aspect of the invention, step 540 involves providing conditions under which the transition metal oxide coating acts as a catalyst for the oxidation of deposited carbon. For example, step 540 may include the application of heat or placing the calibration standard in air. In a still further aspect of the invention, step 540 involves irradiating the transition metal oxide containing coating with ultraviolet light.

Step 540 may take place inside or outside the scanning electron microscope. In one aspect of the invention, step 540 takes place in the scanning electron microscope. In another aspect of the invention, step 540 takes place during calibration scanning. In a further aspect of the invention, step 540 takes place with the calibration standard outside the scanning electron microscope.

Where step 540 takes place during calibration scanning, carbon may never actually accumulate on the calibration standard. Nonetheless, carbon depositing on the calibration standard is still being oxidized—it is being oxidized as quickly as it deposits.

Flowing a current through the transition metal oxide containing coating or setting the transition metal oxide coating to a positive potential during calibration scanning may affect the calibration measurement. To determine whether such an affect is present for a particular calibration standard in a particular SEM system in a particular mode of operation, the calibration scan may be run with and without the flowing current or the positive potential. If the calibration measurement is significantly affected, the step of remove deposited carbon may be postponed until after the calibration measurement has been completed.

Catalytic removal of deposited carbon may take place in the electron beam chamber and in some cases during electron beam scanning. Where the transition metal oxide is a photocatalyst, the SEM system may be provided with an ultraviolet light. However, this is not necessary as photocatalytic activity generally continues for a period of time after a photocatalyst has been exposed to ultraviolet light with an energy above the band gap energy.

Although the invention has been shown and described with respect to a certain preferred embodiment or embodiments, it is obvious that equivalent alterations and modifications will occur to others skilled in the art upon reading and understanding this specification and the annexed drawings. In particular regard to the various functions performed by the above described components (systems, devices, etc.), the terms used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application. Furthermore, to the extent that the term "includes" is used in either the detailed description or the claims, such term is intended to be inclusive in a manner similar to the term "comprising."

What is claimed is:

1. A method of calibrating a SEM system, comprising:
   obtaining a calibration measurement by employing the SEM system to measure a dimension of a feature of a calibration standard, wherein the feature comprises a coating comprising a transition metal oxide selected from the group consisting of $TiO_2$, $Cr_2O_3$, $CrO_3$, $MoO_2$, $MoO_3$, $WO_2$, $WO_3$, $MnO_2$, $MnO_3$, $Fe_2O_3$, $Co_3O_4$, NiO, CuO, ZnO, $In_2O_3$, SnO, and $SnO_2$; and
   using the calibration measurement to calibrate the SEM system.

2. The method of claim 1, wherein using the calibration measurement to calibrate the SEM comprises adjusting the SEM system based on the calibration measurement.

3. The method of claim 1, wherein using the calibration measurement to calibrate the SEM comprises:
   obtaining a sample measurement by employing the SEM system in measuring a dimension of a sample; and
   interpreting the sample measurement with the aide of the calibration measurement.

4. The method of claim 1, wherein the feature is formed of the coating comprising a transition metal oxide.

5. The method of claim 1, wherein the feature comprises a second material and the coating comprising a transition metal oxide forms a coating over the second material.

6. The method of claim 5, wherein the coating has a thickness from about 1 nm to about 100 nm.

7. The method of claim 1, further comprising flowing a current through the calibration standard to oxidize carbon deposits on the calibration standard.

8. The method of claim 1, further comprising setting the coating a positive potential to electrochemically induce oxidation of carbon deposits on the calibration standard.

9. The method of claim 1, further comprising exposing the calibration standard to ultraviolet light to induce oxidation of deposits on the calibration standard.

10. A method of calibrating a SEM system, comprising:
    obtaining a calibration measurement by employing the SEM system to measure a dimension of a feature of a calibration standard, wherein the feature comprises a coating comprising a transition metal oxide selected from the group consisting of $TiO_2$, $Cr_2O_3$, $CrO_3$, $MoO_2$, $MoO_3$, $WO_2$, $WO_3$, $MnO_2$, $MnO_3$, $Fe_2O_3$, $Co_3O_4$, NiO, CuO, ZnO, $In_2O_3$, SnO, and $SnO_2$, the coating having a thickness from about 1 nm to about 100 nm; and
    using the calibration measurement to calibrate the SEM system.

11. The method of claim 10, wherein using the calibration measurement to calibrate the SEM comprises adjusting the SEM system based on the calibration measurement.

12. The method of claim 10, wherein using the calibration measurement to calibrate the SEM comprises:
    obtaining a sample measurement by employing the SEM system in measuring a dimension of a sample; and
    interpreting the sample measurement with the aide of the calibration measurement.

13. The method of claim 10, wherein the feature is formed of the coating comprising a transition metal oxide.

14. The method of claim 10, wherein the feature comprises a second material and the coating comprising a transition metal oxide forms a coating over the second material.

15. The method of claim 10, further comprising flowing a current through the calibration standard to oxidize carbon deposits on the calibration standard.

16. The method of claim 10, further comprising setting the coating a positive potential to electrochemically induce oxidation of carbon deposits on the calibration standard.

17. The method of claim 10, further comprising exposing the calibration standard to ultraviolet light to induce oxidation of deposits on the calibration standard.

18. A method of calibrating a SEM system, comprising:
    obtaining a calibration measurement by employing the SEM system to measure a dimension of a feature of a calibration standard, wherein the feature comprises a coating comprising a transition metal oxide selected from the group consisting of $TiO_2$, $Cr_2O_3$, $CrO_3$, $MoO_2$, $MoO_3$, $WO_2$, $WO_3$, $MnO_2$, $MnO_3$, $Fe_2O_3$, $Co_3O_4$, NiO, CuO, ZnO, $In_2O_3$, SnO, and $SnO_2$;
    flowing a current through the calibration standard to oxidize carbon deposits on the calibration standard; and
    using the calibration measurement to calibrate the SEM system.

19. The method of claim 18, wherein using the calibration measurement to calibrate the SEM comprises adjusting the SEM system based on the calibration measurement.

20. The method of claim 18, wherein using the calibration measurement to calibrate the SEM comprises:
    obtaining a sample measurement by employing the SEM system in measuring a dimension of a sample; and
    interpreting the sample measurement with the aide of the calibration measurement.

21. The method of claim 18, wherein the feature is formed of the coating comprising a transition metal oxide.

22. The method of claim 18, wherein the feature comprises a second material and the coating comprising a transition metal oxide forms a coating over the second material.

23. The method of claim 18, wherein the coating has a thickness from about 1 nm to about 100 nm.

24. The method of claim 18, further comprising setting the coating a positive potential to electrochemically induce oxidation of carbon deposits on the calibration standard.

25. The method of claim 18, further comprising exposing the calibration standard to ultraviolet light to induce oxidation of deposits on the calibration standard.

* * * * *